US007558631B2

(12) United States Patent
Cowan et al.

(10) Patent No.: US 7,558,631 B2
(45) Date of Patent: *Jul. 7, 2009

(54) LEADLESS TISSUE STIMULATION SYSTEMS AND METHODS

(75) Inventors: Mark W. Cowan, Fremont, CA (US); Debra S. Echt, Woodside, CA (US); Richard E. Riley, Palo Alto, CA (US); Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 184 days.

This patent is subject to a terminal disclaimer.

(21) Appl. No.: 11/535,857

(22) Filed: Sep. 27, 2006

(65) Prior Publication Data

US 2007/0078490 A1    Apr. 5, 2007

Related U.S. Application Data

(63) Continuation-in-part of application No. 11/315,023, filed on Dec. 21, 2005.

(60) Provisional application No. 60/689,606, filed on Jun. 9, 2005, provisional application No. 60/639,027, filed on Dec. 21, 2004, provisional application No. 60/639,037, filed on Dec. 21, 2004.

(51) Int. Cl.
*A61N 1/368* (2006.01)

(52) U.S. Cl. .................. 607/122; 607/123; 607/129; 128/898

(58) Field of Classification Search ............. 607/33, 607/57, 122, 123, 129; 128/898
See application file for complete search history.

(56) References Cited

U.S. PATENT DOCUMENTS 3,659,615 A    5/1972    Enger (Continued)

FOREIGN PATENT DOCUMENTS

| DE | 4330680 | 3/2005 |
|---|---|---|
| WO | WO 99/61058 | 12/1999 |
| WO | WO 03/070323 | 8/2003 |

OTHER PUBLICATIONS

Abraham et al., for the Miracle study group, "Cardiac Resynchronization in Chronic Heart Failure," *N Engl J Med*, 2002;346:1845-53.
ACC/AHA Task Force on Practice Guidelines, "Evaluation and Management of Chronic Heart Failure in the Adult," *JACC* 2002;38:2101-13.

(Continued)

*Primary Examiner*—George Manuel
*Assistant Examiner*—Christopher A Flory
(74) *Attorney, Agent, or Firm*—Townsend and Townsend and Crew LLP (57) ABSTRACT

Systems including an implantable receiver-stimulator and an external controller-transmitter system are used for leadless acute stimulation of the heart, particularly after heart surgery. Cardiac pacing and arrhythmia control is accomplished with one or more implantable receiver-stimulators and an external system that alternatively includes the use of an external pacemaker. Receiver-stimulators are implanted in the heart during surgery or during an acute interventional procedure and then a triggered for stimulation by using the external system. In one embodiment of these systems, a controller-transmitter is activated by an external pacemaker to time the delivery of acoustic energy transmission through the body to a receiver-stimulator at a target tissue location. The receiver-stimulator converts the acoustic energy to electrical energy for electrical stimulation of the heart tissue.

46 Claims, 2 Drawing Sheets

U.S. PATENT DOCUMENTS

| | | | |
|---|---|---|---|
| 3,693,627 A | 9/1972 | Berkovits | |
| 3,698,398 A | 10/1972 | Berkovits | |
| 3,735,756 A | 5/1973 | Richards et al. | |
| 3,832,994 A | 9/1974 | Bicher et al. | |
| 3,857,382 A | 12/1974 | Williams et al. | |
| 3,939,844 A | 2/1976 | Peuignot | |
| 3,942,534 A | 3/1976 | Allen et al. | |
| 4,181,133 A | 1/1980 | Kolenik et al. | |
| 4,256,115 A | 3/1981 | Bilitch | |
| 4,265,228 A | 5/1981 | Zoll | |
| 4,280,502 A | 7/1981 | Baker, Jr. et al. | |
| 4,561,442 A | 12/1985 | Vollmann et al. | |
| 4,577,633 A | 3/1986 | Berkovits et al. | |
| 4,651,716 A | 3/1987 | Forester et al. | |
| 4,690,144 A | 9/1987 | Rise et al. | |
| 4,830,006 A | 5/1989 | Haluska et al. | |
| 5,018,523 A | 5/1991 | Bach, Jr. et al. | |
| 5,063,928 A | 11/1991 | Grevis | |
| 5,103,129 A | 4/1992 | Slayton et al. | |
| 5,113,859 A | 5/1992 | Funke | |
| 5,165,403 A | 11/1992 | Mehra | |
| 5,170,784 A | 12/1992 | Ramon | |
| 5,174,289 A | 12/1992 | Cohen | |
| 5,193,539 A | 3/1993 | Schulman et al. | |
| 5,292,338 A | 3/1994 | Bardy | |
| 5,377,166 A | 12/1994 | Kuhn | |
| 5,405,367 A | 4/1995 | Schulman et al. | |
| 5,411,535 A | 5/1995 | Fujii et al. | |
| 5,433,731 A | 7/1995 | Hoegnelid et al. | |
| 5,674,251 A | 10/1997 | Combs et al. | |
| 5,749,909 A | 5/1998 | Schroeppel et al. | |
| 5,751,539 A | 5/1998 | Stevenson et al. | |
| 5,757,104 A | 5/1998 | Getman et al. | |
| 5,766,227 A | 6/1998 | Nappholz et al. | |
| 5,800,464 A | 9/1998 | Kieval | |
| 5,814,089 A | 9/1998 | Stokes et al. | |
| 5,817,130 A | 10/1998 | Cox et al. | |
| 5,844,349 A | 12/1998 | Oakley et al. | |
| 5,871,506 A | 2/1999 | Mower | |
| 5,935,158 A | 8/1999 | Holmstrom et al. | |
| 5,978,204 A | 11/1999 | Stevenson | |
| 5,998,910 A | 12/1999 | Park et al. | |
| 6,037,704 A | 3/2000 | Welle | |
| 6,070,101 A | 5/2000 | Struble et al. | |
| 6,078,837 A | 6/2000 | Peterson et al. | |
| 6,110,098 A | 8/2000 | Renirie et al. | |
| 6,223,079 B1 | 4/2001 | Bakels et al. | |
| 6,233,484 B1 | 5/2001 | Ben-Haim et al. | |
| 6,330,475 B1 | 12/2001 | Renirie et al. | |
| 6,366,816 B1 | 4/2002 | Marchesi | |
| 6,408,205 B1 | 6/2002 | Renirie et al. | |
| 6,424,234 B1 | 7/2002 | Stevenson | |
| 6,439,236 B1 | 8/2002 | Porter et al. | |
| 6,445,953 B1 | 9/2002 | Bulkes et al. | |
| 6,527,729 B1 * | 3/2003 | Turcott | 600/528 |
| 6,534,895 B2 | 3/2003 | Kadota et al. | |
| RE38,119 E | 5/2003 | Mower | |
| 6,628,989 B1 | 9/2003 | Penner et al. | |
| 6,645,145 B1 | 11/2003 | Dreschel et al. | |
| 6,647,292 B1 | 11/2003 | Bardy et al. | |
| 6,654,638 B1 | 11/2003 | Sweeny | |
| 6,671,547 B2 | 12/2003 | Lyster et al. | |
| 6,707,230 B2 | 3/2004 | Smith et al. | |
| 6,721,597 B1 | 4/2004 | Bardy et al. | |
| 6,728,576 B2 * | 4/2004 | Thompson et al. | 607/30 |
| 6,754,528 B2 | 6/2004 | Bardy et al. | |
| 6,754,531 B1 | 6/2004 | Kroll et al. | |
| 6,764,446 B2 | 7/2004 | Wolinsky et al. | |
| 6,788,974 B2 | 9/2004 | Bardy et al. | |
| 6,834,204 B2 | 12/2004 | Osteroff et al. | |
| 6,856,835 B2 | 2/2005 | Bardy et al. | |
| 6,970,742 B2 | 11/2005 | Mann et al. | |
| 7,010,350 B2 | 3/2006 | Kralik | |
| 7,043,292 B2 | 5/2006 | Tarjan et al. | |
| 7,200,437 B1 | 4/2007 | Nabutovsky et al. | |
| 7,283,874 B2 * | 10/2007 | Penner | 607/33 |
| 7,349,740 B2 * | 3/2008 | Soykan et al. | 607/50 |
| 2002/0077673 A1 | 6/2002 | Penner et al. | |
| 2003/0013974 A1 * | 1/2003 | Natarajan et al. | 600/481 |
| 2003/0069625 A1 | 4/2003 | Ley et al. | |
| 2004/0015104 A1 | 1/2004 | Goldberger | |
| 2004/0167580 A1 | 8/2004 | Mann et al. | |
| 2004/0172083 A1 | 9/2004 | Penner | |
| 2004/0204744 A1 | 10/2004 | Penner et al. | |
| 2004/0260346 A1 * | 12/2004 | Overall et al. | 607/4 |
| 2006/0009831 A1 * | 1/2006 | Lau et al. | 607/129 |
| 2006/0106442 A1 * | 5/2006 | Richardson et al. | 607/119 |
| 2006/0135999 A1 * | 6/2006 | Bodner et al. | 607/4 |
| 2006/0136004 A1 | 6/2006 | Cowan et al. | |
| 2006/0224067 A1 * | 10/2006 | Giftakis et al. | 600/483 |
| 2006/0241701 A1 * | 10/2006 | Markowitz et al. | 607/5 |
| 2007/0032749 A1 * | 2/2007 | Overall et al. | 600/595 |
| 2007/0088394 A1 * | 4/2007 | Jacobson | 607/4 |
| 2007/0088397 A1 * | 4/2007 | Jacobson | 607/9 |
| 2007/0088398 A1 * | 4/2007 | Jacobson | 607/9 |
| 2007/0150009 A1 * | 6/2007 | Kveen et al. | 607/9 |
| 2007/0232936 A1 * | 10/2007 | Mann et al. | 600/486 |
| 2007/0260286 A1 * | 11/2007 | Giftakis et al. | 607/9 |
| 2007/0265677 A1 * | 11/2007 | Giftakis et al. | 607/45 |

OTHER PUBLICATIONS

Allessie et al., "Regional Control of Atrial Fibrillation by Rapid Pacing in Conscious Dogs," *Circulation* 1991;84:1689-97.

Ansalone et al., "Bi-ventricular Pacing I Heart Failure:Back to Basics in the Pathophysiology of Left Bundle Branch Block to Reduce the Number of Nonresponders," *Am J Cardiol* 2003;91:55F-61F.

Auricchio et al., "Cardiac Resynchronization Therapy: Current State of the Art," *Circulation* 2004;109:300-307.

Bardy et al., "The Totally Subcutaneous ICD System (The S-ICD)," *PACE*. 2002; 24,578.

Becker et al, "Suppression of Atrial Fibrillation by Multisite and Septal Pacing in a Novel Experimental Model", *Cardiovascular Research* 2001;54(2):476-481.

Bradley et al., "Cardiac Resynchronization and Death from Progressive Heart Failure: A Meta-Analysis of Randomized Controlled Trials," *JAMA* 2003;289:730-740.

Camm et al., Chapter 6: Nonpharmaceutical treatment of atrial fibrillation, In *Atrial Fibrillation. Facts from Yesterday—Ideas for tomorrow*. Futura Publishing Company, Inc., Armonk, NY, 1994, pp. 125-147.

Dalecki et al., "Effects of Pulsed Ultrasound on the Frog Heart: I. Thresholds for Changes in Cardiac Rhythm and Aortic Pressure," *Ultrasound in Med. & Biol*. 1993; 19:385-390.

Dalecki et al., "Effects of Pulsed Ultrasound on the Frog Heart: II. An Investigation of Heating as a Potential Mechanism," *Ultrasound in Med. & Biol*. 1993; 19:391-398.

Dalecki et al., "Thresholds for premature ventricular contractions in frog hearts exposed to lithotripter fields," *Ultrasound in Med. & Biol*. 1991; 17:341-346.

Daoud et al., " Implantation Techniques and Chronic Lead Parameters of Biventricular Pacing Dual-chamber Defibrillators," *J Cardiovasc Electrophysiology* 2002; 13:964-970.

Daubert et al., "Permanent Left Ventricular Pacing With Transvenous Leads Inserted Into The Coronary Veins," *PACE* 1998;21;239-245.

Daubert et al., "Use of Specifically Designed Coronary Sinus Leads for Permanent Left Ventricular Pacing: Preliminary Experience," *PACE*, 1997; 20: II-NASPE Abstract Apr. 17, 1997.

David Trial Investigators, "The Dual Chamber and VVI Implantable Defibrillator (David) Trial," *JAMA* 2002;288:3115-3123.

Deshmukh et al. "Direct His-bundle pacing: present and future," *PACE* 2004;27 [Pt.II]:862-70.

Ellenbogen et al., "Detection and Management of An Implantable Cardioverter Defibrillator Lead Failure," *JACC*. 2003;41:73-80.

Feldman et al, "Comparison of medical therapy, resynchronization and defibrillation therapies in heart failure trial (Companion)," Presented at ACC 2003 Late Breaking Clinical Trials, 1 page.

Franz, "Mechano-electrical feedback in ventricular myocardium," *Cardiovascular Research*. 1996; 32:15-24.

Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). *Circulation*. 2002; 106:2145-2161.

Hu et al., "Stretch-Activated Ion Channels in the Heart," *J. Mol. Cell Cardiol*. 1997; 29:1511-1523.

Johnson et al., "Adaptive Pacing During Ventricular Fibrillation," *PACE* 2003;26:1824-36.

Kalman J.M. et al, "Regional Entrainment of Atrial Fibrillation in Man", *J Cardiovasc Electrophysiol* 1991;7:867-76.

Kass et al., "Improved Left Ventricular Mechanics from Acute VDD Pacing in Patients with Dilated Cardiomyopathy and Ventricular Conduction Delay," *Circulation* 1999;99:1567-73.

Kenknight B.H. et al, "Regional Capture of Fibrillating Ventricular Myocardium" Circ Res 1999;77:849-55.retrieve from the Internet: <<http://circres.ahajournals.org/cgi/content/full/77/4/849>>.

Kohl et al., Stretch-Induced Changes in Heart Rate and Rhythm: Clinical Observations, Experiments and Mathematical Models. *Progress in Biophysics & Molecular Biology*, 1999;71:91-138.

Kohl et al., "Sudden Cardiac Death by Commotio Cordis: Role of Mechano-Electrical Feedback," *Cardiovascular Research*, 2001; 50:280-289.

Leclercq et al, "Is Dual Site Better than Single Site Atrial Pacing in the Prevention of Atrial Fibrillation?" *PACE* 2000;23:2102-7.

Leclercq et al., "Systolic Improvement and Mechanical Resynchronization does not Require Electrical Synchrony in the Dilated Failing Heart with Left Bundle-Branch Block", *Circulation* 2002;106:1760-1763.

Leclerq et. al., "Acute Hemodynamic Effects of Biventricular DDD Pacing in Patients with End-Stage Heart Failure", JACC 1998;32:1825-1831.

Lee et al., "Effect of implantable Defibrilators of Arrhythmic Events and Mortality in the Multicenter Unsustained Tachycardia Trial," *Circulation*. 2002; 106:233-238.

Linde et al., "Long-Term Benefits of Biventricular Pacing in Congestive Heart Failure: From the Multisite Stimulation in Cardiomyopathy (MUSTIC) Study", *J Am Coll Cardiol* 2002;40:111-118.

Miracle Trial Investigators, "Combined Cardiac Resynchronization and Implantable Cardioversion Defibrillation in Advanced Heart Failure: the Miracle ICD Trial," *JAMA* 2003;289:2685-2694.

Mirza et al, "Biatrial Pacing for Paroxysmal Atrial Fibrillation", *J Am Coll Cardiol* 2002;40:457-463.

Moss et al., "Prophylactic Implantation of a Defibrillator in Patients with Myocardial Infarction and Reduced Ejection Fraction," *N Engl J Med*. 2002; 346:877-933.

Niehaus et al., "Non-Contact Cardiac Stimulation with locused Ultrasound Pulses," *PACE* 2003: 26:1023.

Nielsen et al., "A Randomized Comparison of Atrial and Dual-Chambered Pacing in 177 Consecutive Patients With Sick Sinus Syndrome," *J AM Coll Cardiol* 2003;42:614-623.

Nolte et al., "Mechanically Induced Ventricular Extrasystoles in the Isolated Perfused Guinea-Pig Heart," *Arzneim.-Forsch/Drug Research*. 1987; 37(11): 1025-1029.

Peschar et al., "Left Ventricular Septal and Apex Pacing for Optimal Pump Function in Canine Hearts," *J Am Coll Cardiol*, 2003;41:1218-26.

Reiter et al.., "Effects of Mechano-Electrical Feedback: Potential Arrhythmogenic Influence in Patients With Congestive Heart Failure," *Cardiovascular Research*, 1996; 32:44-51.

Smailys et al., "Investigation of the Possibilities of cardiac Defibrillation by Ultrasound," *Resuscitation*, 1981; 9:233-242.

Sowton, "Clinical Results with the Tachylog Antitachycardia Pacemaker", *PACE* 1984; 7(Part II):1313-1317.

Tacker, Chapter 1: Fibrillation causes and criteria for defibrillation. In *Defibrillation of the Heart. Taker*, WA, ed. Mosby-Year Book, Inc., St. Louis, Missouri, 1994, pp. 1-14.

The Antiarrhythmics Versus Implantable Defibrillators (AVID) Investigators, "A Comparison of Antiarrhythmic Drug Therapy with Implantable Defibrillators in Patients Resuscitated fron Near Fatal Ventricular Arrhythmias," *N Engl J Med*, 1997;337: 1576-1583.

Valls-Bertault et al., "Adverse Events with Transvenous Left Ventricular Pacing in Patients with Severe Heart Failure: Early Experience from a Single Centre," *Europace*, 2001;3:60-63.

Warren et al., "Clinical Evaluation of Automatic Tachycardia Diagnosis by an Implanted Device", *PACE* 1986;9 (Part II):1079-1083.

International Search Report and Written Opinion of PCT Application No. PCT/US2007/076812, mailed Apr. 7, 2008, 8 pages total.

International Search Report and Written Opinion of PCT Application No. PCT/US05/46532, dated Jun. 23, 2008, 8 pages total.

* cited by examiner

LEADLESS TISSUE STIMULATION SYSTEMS AND METHODS

CROSS-REFERENCES TO RELATED APPLICATIONS

This application is a continuation-in-part of U.S. patent application Ser. No. 11/315,023, filed on Dec. 21, 2005, and claims the benefit and priority of the following: U.S. Provisional Application No. 60/689,606, filed on Jun. 9, 2005; U.S. Provisional Application No. 60/639,027, filed on Dec. 21, 2004; and U.S. Provisional Patent Application No. 60/639,037, filed on Dec. 21, 2004, the full disclosures of which are incorporated herein by reference.

BACKGROUND OF THE INVENTION

1. Field of the Invention

The systems and methods of this invention relate to electrical stimulation of the heart by means of an implantable device. Specifically, the present invention relates to systems and methods for providing such stimulation without the use of conventional lead/electrode systems. More specifically, the present application provides systems and methods for treatment of heart failure and for terminating heart arrhythmias using external and implantable pacing systems and components.

Electrical stimulation of body tissues is used throughout medicine for treatment of both chronic and acute conditions. A commonly implanted device utilizing electrical stimulation is the cardiac pacemaker. External cardiac pacemakers are also commonly used in acute settings, particularly after cardiac surgery or in emergency situations to provide stimulation of the heart during recovery.

Devices to provide temporary, acute heart stimulation comprise an external pulse generator (EPG), i.e., an external pacemaker, which is connected to leads/wires that have been placed in or on the heart. This invention pertains to devices in which at least one portion providing direct electrical stimulation to the body tissue is either permanently or temporarily implanted in the heart and is controlled by one or more external devices.

EPG devices are connected to electrode/lead wires that have been placed in one or more heart chambers by vascular access or surgical access or placed on the outside (epicardial surface) of the heart during surgical access. Surgical access is accomplished using an open chest procedure or as a minimally invasive procedure. Following heart surgery, it is common for these wires to be placed as a precaution against post surgical arrhythmias and used either to stimulate the heart to maintain a heart rhythm or to terminate abnormal rhythms (e.g., tachyarrhythmias in the atria or ventricles). These wires protrude from the body either near the vascular insertion site or through a chest insertion site left after closure of the surgical procedure. The insertion/exit site of the wire from the patient must be kept sterile. The temporary, acute use of the EPG and wires is referred to as temporary pacing and is used for a variable period; some times up to as long as 10 days. The pacing wires are removed after the patient has stabilized. In patients who require ambulatory pacing for longer periods, an implanted pacemaker and pacemaker leads are used and this approach is generally referred to as permanent pacing. The use of temporary lead wires or pacing leads is associated with significant problems such as complications due to infection, lead failure, and electrode/lead dislodgement.

The requirement for leads in order to accomplish stimulation also limits the number of accessible locations in the body. For example, temporary leads are not placed using arterial access due to the increased risks associated with thrombus, thromboemboli, and embolization in the arterial vascular system. The requirement for leads/wires has also limited the ability to stimulate at multiple sites (multi-site stimulation), which requires even more wires protruding from the body, thus increasing complication risks.

An EPG is a pacemaker that is a battery-powered electronic device typically located and used at the bedside of a patient in need of emergency heart stimulation or as a precaution in treating arrhythmias and heart stimulation needs after surgery, As noted above, the EPG is connected to the heart by an insulated metal lead wire with distal electrodes The wires are connected to terminals at the EPG, which functions in commonly used single and dual chamber pacemaker modes and also in commonly used anti-arrhythmia pacing modalities. Pacemakers were initially developed for and are most commonly used to treat bradycardia, slow heart rates, which may result from a number of conditions, particularly following surgery. More recently, advancements in pacemaker complexity, and associated sensing and pacing algorithms have allowed progress in using pacemakers for the treatment of other conditions, notably heart failure (HF) and fast heart rhythms (tachyarrhythmia/tachycardia). EPGs contain the same or similar operational characteristics as implanted pacemakers including sensing circuits to determine the intrinsic heart activity and adjustments for pacing rate, pace pulse amplitude, pace pulse duration, sensitivity levels for detecting heart beats, pacing modalities, anti-tachyarrhythmia algorithms, and the like.

In a common application such systems can be either single chamber with a lead wire placed in or on either the right atrium or right ventricle, or dual chamber systems with one lead wire placed in or on the right atrial wall and a second lead placed in or on the right ventricular wall. For the treatment of HF, through what is commonly known as cardiac resynchronization therapy, bi-ventricular pacing is utilized, requiring that an additional lead be placed in contact with the left ventricle. Using a vascular access to the left ventricle, the third lead is typically advanced into the right atrium, into the orifice of the coronary sinus, and then maneuvered through the coronary sinus veins to a position on the epicardial aspect of the posteriolateral or lateral wall of the left ventricle, alternatively the third lead is placed epicardially directly in contact on the wall of the left ventricle using a surgical access. Particularly in temporary pacing situations following surgery, the leads/wires are placed on the epicardial aspects of the heart chambers.

A common and difficult problem with using temporary pacing leads is infection. Infections can occur locally at the open skin of the insertion site or can progress down the wire and develop more serious systemic internal infections including pericarditis or endocarditis. Some other common complications in using temporary wires are dislodgement of the lead from the tissue and perforation of the myocardium by the lead/wire.

It has recently been found that biventricular pacing following surgery can help to optimize hemodynamics during the recovery period. This is particularly pertinent in cardiac surgery patients with wall-motion abnormalities and in patients with symptoms of HF. Placement of the third lead to contact the left ventricle remains a significant problem using a vascular access. In cardiac surgery patients, access to the heart allows a direct epicardial attachment of a left ventricular lead. The vascular approach to left ventricle access is not often used for temporary pacing due to the difficulty of the lead placement. The coronary sinus is a complicated venous pathway with multiple branches which bend and narrow with considerable variation as they extend distally onto the epicardium of the left ventricle. Placement of the third lead requires significant skill on the part of the physician. In order to provide adequate steerability and pushability, the design of the left ventricular lead or a lead introduction system/device is much more complicated than regular temporary pacing leads/wires. Often the positioning and placement of the left ventricular lead can take over an hour to perform, exposing the patient to increased fluoroscopy radiation, increased anesthesia exposure, and increased procedure risks.

Left ventricular leads are not placed inside the heart chamber as they are for the right-ventricular leads for several reasons. They would have to be situated retrograde across the aortic valve or trans-septally across the mitral valve which could cause aortic or mitral valvular insufficiency. The patients would be subject to risk of thromboembolic complications from having leads in the arterial circulation. Alternatively, atrial transeptal puncture from the right atrium to insert a pacing lead into the left atrium or left ventricle is also subject to risks of thromboembolic complications and for left ventricular sites, would cause mitral regurgitation. Moreover, all temporary pacemaker leads/wires are associated with an incidence of infection, and the risk of valvular endocarditis is greater in the left heart.

In patients receiving a bi-ventricular pacing system, site selection for placement of the left ventricular lead has been found to be critically important in order to provide improved hemodynamic benefit. Up to 40% of patients receiving bi-ventricular pacing for the treatment of HF do not benefit from the pacing (i.e., hemodynamic measures and HF functional class do not improve or deteriorate). The most important cause for lack of benefit is thought by experts to be due to suboptimal or incorrect left ventricular stimulation site. The ability to precisely select the left ventricular site for stimulation in combination with right ventricular stimulation, would aid in the improvement of hemodynamic benefits following cardiac surgery.

Moreover, left ventricular stimulation currently is restricted to sites on the epicardial (outer) surface of the heart; the coronary sinus courses on the epicardium, and surgically implanted left ventricular leads/wires are screwed into the epicardium. Recent data indicates that endocardial (inside lining) or subendocardial (inside layer) stimulation sites in the left ventricle provide additional hemodynamic benefit.

Importantly, clinical trial data now suggest that pacing of the left ventricle alone may result in hemodynamic benefit equivalent to that of bi-ventricular pacing. Thus, a leadless pacing system has the potential to accomplish the benefit of bi-ventricular pacing without the need for a right ventricular pacing lead or electrodes.

It would also be beneficial to provide more physiological right ventricular pacing for patients to improve hemodynamics following cardiac surgery. In normal physiology, the right ventricle is first stimulated in the upper septal area, and then the impulse travels down specially conducting pathways near the endocardium to the right ventricular apex. However, using a vascular-placed lead/wire, pacing the right ventricle is virtually always accomplished from a lead tip electrode located in the right ventricular apex, such that the subsequent conduction pathway is abnormal and slow. In similar reference to abnormal conduction from the left-sided epicardial stimulation, leads/wires placed surgically on the right ventricle also impact hemodynamic performance. Clinical trials have recently shown that in patients with and without A-V block, pacing from the right ventricular apex can result in increased total mortality and re-hospitalization for heart failure. Thus, it would be advantageous to be able to pace the right ventricle at more physiological locations such as the endocardial aspects of upper septum. The most appropriate physiological location to pace the ventricle in patients with sinus nodal or A-V junction conduction disease is to directly pace the His bundle. In patients with lower conduction disease involving the A-V junction or bundle branches, the most physiological pacing sites have been found to be the left ventricular septum or left ventricular apex. These are locations in proximity to the specialized Purkinje conduction network. These locations are not accessible using current transvenous lead-based pacing systems. It would be advantageous to be able to select the pacing site in order to model more normal conduction and improve hemodynamics following cardiac surgery.

In addition to improving hemodynamics, post cardiac surgery patients often have arrhythmias. Pacing algorithms have been shown to be effective in terminating atrial and ventricular arrhythmias, referred to as antitachycardia pacing (ATP). For ATP, the lead-based system has limitations in selecting the location of the pacing application, particularly in the left side of the heart. Ventricular tachyarrhythmias can be readily terminated using low voltage pacing stimulation if the site of the pacing is near the ventricular tachycardia focus or reentrant circuit. However, this is usually in the left ventricle, and close to the endocardium. As noted above, current temporary pacing devices incorporate antitachycardia pacing modalities, but the pacing site is limited to the right atrial or right ventricular lead or is subject to the same limitations previously described for left-sided lead placements. Further, right-sided locations have been shown to be less effective in electrophysiology laboratory testing, especially for tachyarrhythmias of high rate which are more serious. This ineffective treatment may lead to treating the patient with high-energy cardioversion/defibrillation shocks using an externally applied defibrillator. These high energy shocks are extremely painful and place additional stress on post cardiac surgery patients. Therefore, it would be advantageous to be able to select the pacing site, particularly for ventricular tachyarrhythmias near the endocardium and in the left ventricle. Having the capability to select the location for a left ventricular electrode for terminating episodes of ventricular tachycardia using antitachycardia pacing techniques would be expected to be more effective compared to current devices.

Another limitation of both the requirement of having leads and of having limited access to the left heart is in the emerging area of multisite pacing for termination of atrial fibrillation (AF) and ventricular fibrillation (VF). These arrhythmias typically arise in and are maintained by the left atrium and left ventricle. Studies have demonstrated the presence of excitable gaps within the tissue during atrial fibrillation (animal and human studies) and ventricular fibrillation (animal studies). By placing and stimulating at multiple pacing sites, regional pacing capture can be obtained during these arrhythmias. This means that if stimulation is delivered at the appropriate timing to a sufficient number of sites, in the appropriate locations, termination of atrial and ventricular fibrillation is possible. The advantage of terminating fibrillation with selected site left ventricular pacing would be the avoidance of painful high energy shocks. In this application the capability for left-sided stimulation and multi-sites of stimulation would be advantageous.

In addition to the termination of tachyarrhythmias, pacemaker algorithms have been used to prevent tachyarrhythmias. In post cardiac surgery patients AF is a typical complication. In patients receiving permanent pacemakers, the dual chamber (DDD) mode has been shown to result in fewer episodes of AF compared to single chamber (VVI) mode in several large clinical trials. DDD pacing that incorporates simultaneous multisite stimulation of both the high right atrium and CS ostium has also been compared to standard single atrial site DDD pacing for the suppression of AF, showing a modest reduction of AF episodes. Atrial stimulation at a site or multiple sites may be advantageous for the prevention of atrial fibrillation by shortening total atrial activation time. Right atrial sites in Koch's triangle and Bachman's bundle may reduce atrial activation time by stimulating near or within atrial conduction tracts or within other tracts that are part of the normal conduction pathway. In an experimental canine model (Becker), either 4 pacing sites (2 in RA and 2 in LA) or one in the interatrial septum were required for suppression of AF. While these results are very promising, they present a technical obstacle for current pacemaker systems. The use of multisite pacing incorporating pacing sites in the left atrium for the suppression of AF has not been evaluated in humans because of all the issues of using multiple leads and in using leads within the left heart.

It follows that if AF may be suppressed with multisite atrial pacing (especially in the left atrium), then VF may also be suppressed with multisite ventricular pacing (especially in the left ventricle). However, the difficulties associated with the implantation of multiple leads in the left ventricle has rendered this form of prevention almost impossible.

For these reasons, it would be desirable to accomplish stimulation without lead wires. In this application we describe methods and apparatus, using acoustic energy in combination with an implantable leadless stimulator and an external control system that overcome limitations in pacing site selection. In co-pending applications we further describe improved stimulating devices. Methods and systems to evaluate and optimize positioning for implantation of this invention are described herein.

2. Description of the Background Art

U.S. Pat. No. 3,659,615, Enger; Encapsulated Non-Permeable Piezoelectric Powered Pacesetter, May 1972

U.S. Pat. No. 4,256,115, Bilitch; Leadless Cardiac Pacer, March 1981

U.S. Pat. No. 4,690,144, Rise et al.; Wireless Transcutaneous Electrical Tissue Stimulator, September 1987

U.S. Pat. No. 5,170,784, Ramon et al.; Leadless Magnetic Cardiac Pacemaker, December 1992

German Patent DE4330680 (abandoned), Zwicker; Device for Electrical Stimulation of Cells within a Living Human or Animal, March 1995

U.S. Pat. No. 5,405,367, Schulman et al.; Structure and Method of Manufacture of an Implantable Microstimulator, April 1995

U.S. Pat. No. 5,411,535, Fujii et al.; Cardiac Pacemaker Using Wireless Transmission, May 1995

U.S. Pat. No. 5,749,909, Schroeppel et al.; Transcutaneous Energy Coupling Using Piezoelectric Device, May 1998

U.S. Pat. No. 5,751,539, Stevenson et al.; EMI Filter for Human Implantable Heart Defibrillators and Pacemakers, May 1998

U.S. Pat. No. 5,766,227, Nappholz et al.; EMI Detection in an Implantable Pacemaker and the like, May 1998

U.S. Pat. No. 5,814,089, Stokes et al.; Leadless Multisite Implantable Stimulus and Diagnostic System, September 1998

U.S. Pat. No. 5,817,130, Cox et al.; Implantable Cardiac Cardioverter/Defibrillator with EMI Suppression Filter with Independent Ground Connection, October 1998

U.S. Pat. No. 5,978,204, Stevenson; Capacitor with Dual Element Electrode Plates, November 1999

U.S. Pat. No. 6,037,704, Welle; Ultrasonic Power Communication System, March 2000

U.S. Pat. No. 6,366,816, Marchesi; Electronic Stimulation Equipment with Wireless Satellite Units, April 2002

U.S. Patent Application Publication 2002/0077673, Penner et al.; Systems and Methods for Communicating with Implantable Devices, June 2002

U.S. Pat. No. 6,424,234, Stevenson; Electromagnetic Interference (EMI) Filter and Process for Providing Electromagnetic Compatibility of an Electronic Device while in the Presence of an Electromagnetic Emitter Operating at the Same Frequency, July 2002

U.S. Pat. No. 6,445,953, Bulkes et al.; Wireless Cardiac Pacing System with Vascular Electrode-Stents, September 2002

U.S. Pat. No. 6,654,638, Sweeney; Ultrasonically Activated Electrodes, November 2003

U.S. Patent Application Publication 2004/0172083, Penner; Acoustically Powered Implantable Stimulating Device, September 2004

U.S. Pat. No. 4,280,502, Baker, Jr. et al., Tachycardia arrester, July 1981

U.S. Pat. No. 4,561,442, Vollmann et al., Implantable cardiac pacer with discontinuous microprocessor programmable antitachycardia mechanisms and patient data telemetry, December 1985

U.S. Pat. No. 4,181,133, Kolenik et al., Programmable tachycardia pacer, January 1980

U.S. Pat. No. 3,832,994, Bicher et al., Cardiac Monitor, September 1974

U.S. Pat. No. 3,693,627, Berkovits, Stimulator for Treatment of Tachycardia with a Burst of Stimuli Having a Continuously Variable Rate, September 1972

U.S. Pat. No. 3,698,398, Berkovits, Rate-scanning Pacer for Treatment of Tachycardia, October 1972

U.S. Pat. No. 4,577,633, Berkovits et al., Rate scanning demand pacemaker and method for treatment of tachycardia, March 1086

U.S. Pat. No. 5,063,928, Grevis et al., Apparatus and method for detecting and treating cardiac tachyarrhythmias, November 1991

U.S. Pat. No. 3,939,844, Peuignot et al., Method and apparatus for stimulating a heart to eliminate rhythmic abnormalities, especially tachycardias, February 1976

U.S. Pat. No. 3,942,534, Allen et al., Device for terminating tachycardia, March 1976

U.S. Pat. No. 4,830,006, Haluska et al., Implantable cardiac stimulator for detection and treatment of ventricular arrhythmias, May 1989

U.S. Pat. No. 5,674,251, Combs et al., Method and apparatus for treatment of atrial fibrillation, October 1997

U.S. Pat. No. 6,078,837, Peterson et al., Method and apparatus for treatment of fibrillation, June 2000

U.S. Pat. No. 6,754,531, Kroll et al., Anti-tachycardia pacing methods and devices, June 2004

U.S. Pat. No. 6,856,835, Bardy et al., Biphasic waveform for anti-tachycardia pacing for a subcutaneous implantable cardioverter-defibrillator, February 2005

U.S. Pat. No. 6,834,204, Osteroff et al., Method and apparatus for inducing defibrillation in a patient using a T-shock waveform, December 2004

U.S. Pat. No. 6,788,974, Bardy et al., Radian curve shaped implantable cardioverter-defibrillator canister, September 2004

U.S. Pat. No. 6,754,528, Bardy et al. Apparatus and method of arrhythmia detection in a subcutaneous implantable cardioverter/defibrillator, June 2004

U.S. Pat. No. 6,721,597, Bardy et al. Subcutaneous only implantable cardioverter defibrillator and optional pacer, April 2004

U.S. Pat. No. 6,671,547, Lyster et al. Adaptive analysis method for an electrotherapy device and apparatus, December 2003

U.S. Pat. No. 6,647,292, Bardy et al. Unitary subcutaneous only implantable cardioverter-defibrillator and optional pacer, November 2003

U.S. Pat. No. 7,010,350, Kralik, Temporary biventricular pacing of heart after heart surgery, March 2006

Allessie M, Kirchof C, Scheffer G J, Chorro F, Brugado J k "Regional Control of Atrial Fibrillation by Rapid Pacing in Conscious Dogs," *Circulation* 1991; 84:1689-97.

DAVID Trial Investigators, "The Dual Chamber and VVI Implantable Defibrillator (DAVID) Trial," *JAMA* 2002; 288:3115-3123.

Johnson P L, Newton J C, Rollins D L, Smith S M, Ideker R E, "Adaptive Pacing during Ventricular Fibrillation, *PACE* 2003; 26:1824-36.

Kass D A, Chen C-H, Curry C, Talbot M, Berger R, Fetics B, Nevo E, "Improved Left Ventricular Mechanics from Acute VDD Pacing in Patients with Dilated Cardiomyopathy and Ventricular Conduction Delay," *Circulation* 1999; 99:1567-73.

Abraham W T, Fisher W G, Smith A L, Delurgio D B, Leon A R, Loh E, Kocovic D Z, Packer, M, Clavell A L, Hayes D L, Ellestad M, Messenger J, for the MIRACLE study group, "Cardiac Resynchronization in Chronic Heart Failure," N Engl J Med, 2002; 346:1845-53.

Becker R. et al., "Suppression of Atrial Fibrillation by Multisite and Septal Pacing in a Novel Experimental Model", Cardiovascular Research 2001; 54:476-481.

Kalman J. M. et al., "Regional Entrainment of Atrial Fibrillation in Man", J Cardiovasc Electrophysiol 1991; 7:867-76.

KenKnight B. H. et al., "Regional Capture of Fibrillating Ventricular Myocardium" Circ Res 1999; 77:849-55.

Leclercq J. F. et al., "Is Dual Site Better than Single Site Atrial Pacing in the Prevention of Atrial Fibrillation?" PACE 2000; 23"2102-7.

Mirza I. et al., "Biatrial Pacing for Paroxysmal Atrial Fibrillation", J Am Coll Cardiol 2002; 40:457-463.

Sowton, E., "Clinical Results with the Tachylog Antitachycardia Pacemaker", PACE 1984; 7 Part II): 1313-1317.

Warren, J. et al., "Clinical Evaluation of Automatic Tachycardia Diagnosis by an Implanted Device", PACE 1986; 9 (Part II):1079-1083.

Ansalone G, Giannantoni P, Ricci R, Trambaiolo P, Fedele F, Santini M, "Bi-ventricular pacing I heart failure: back to basics in the pathophysiology of left bundle branch block to reduce the number of nonresponders," *Am J Cardiol* 2003; 91:55F-61F.

Auricchio A and Abraham W T, "Cardiac resynchronization therapy: current state of the art," *Circulation* 2004; 109: 300-307.

Deshmukh P M and Romanyshyn M, "Direct His-bundle pacing: present and future,"*PACE* 2004; 27 [Pt. II]:862-70.

Peschar M, de Swart H, Michels K J, Reneman R S, and Prinzen F W, "Left ventricular septal and apex pacing for optimal pump function in canine hearts," *J Am Coll Cardiol* 2003; 41:1218-26.

BRIEF SUMMARY OF THE INVENTION

The present invention provides methods and devices to electrically stimulate cardiac muscle and other body tissue utilizing acoustic energy to transmit both energy and signal information from an external device to an implanted device. The external device, generally referred to as the controller-transmitter or acoustic controller-transmitter, provides appropriate timing and control functions and transmits acoustic energy to the implanted device. The implanted device, generally referred to as the receiver-stimulator, receives the acoustic energy and converts it into electrical energy and applies that electrical energy to stimulating electrodes. The implanted device is adapted to be permanently implanted at a location where it is desired to provide electrical stimulus, with the stimulating electrodes in direct contact with the cardiac muscle or other body tissue. Optionally, two or more receiver-stimulators may be implanted to be controlled by a controller-transmitter.

A cardiac pacemaker employing ultrasonic energy transfer according to the present invention comprises an implantable receiver-stimulator device adapted to be implanted in or attached to any desired location either endocardially, epicardially, or intramyocardially. Various surgical or minimally invasive, transvascular techniques and tools (e.g., injectors, catheters, stylets) can be adapted and used to deliver, place, embed, and secure the receiver-stimulator device to these locations. The receiver-stimulator would additionally be adapted to provide permanent attachment to the implant site including possibly the use of helical coils, barbs, tines, clips, or the like. Design features such as tines or irregularities in surface, or by bonding onto its outer surface materials, which are known to stimulate cellular growth and adhesion, would enhance chronic endothelialization. Alternatively, the receiver-stimulator could be adapted for implantation in the coronary vasculature at preferred sites for stimulation, e.g., incorporated into a stent-like platform suitable for intravascular delivery and deployment. In a specific embodiment, the device could reside on the outer surface of a stent and be held in place between the outer stent wall and the inner vessel wall. Functionally, the receiver-stimulator device comprises 1) an ultrasound transducer to receive the acoustic energy from a controller-transmitter device and transform it into electrical energy, 2) an electrical circuit to transform the alternating electrical energy into a direct current or waveform having other characteristics, and 3) electrodes to transfer electrical energy to the myocardium. The receiver-stimulator would use signal information from the acoustic energy transmission to configure the electrical output, for example, the pulse width of the transmission would determine the pulse duration/width of the electrical output waveform. Additionally, the receiver-stimulator may comprise circuitry for additional control logic, for example, selecting activation of individual receiver-stimulators (on-off control), timing delays, waveform shape adjustments, or the like. In particular, when more than one receiver-stimulator is implanted to be controlled by a single controller-transmitter, the transmitted energy signal may contain addressing or selection information identifying which receiver-stimulator is to be activated at any particular time.

Subsequently, an external controller-transmitter device would be used; this device containing some or most or all the elements of currently available external pacemaker systems, with specific adaptations pertinent to this invention. Such typical pacemaker elements may include a power source, pacemaker control and timing circuitry, a sensing system possibly comprised of cardiac electrogram sensing electronics, motion detectors, body or other temperature sensors, pressure sensors, impedance sensors (e.g., for measuring respiration cycles or lung edema), or other types of physiologic sensors, and signal conditioning and analysis functions for the various electrodes and detectors. Additionally, the controller-transmitter device would contain an ultrasound amplifier and an ultrasound transducer to generate acoustic energy, and transmit such energy from the surface of the body in the general direction of the heart and specifically in the direction of the implanted receiver-stimulator device. The duration, timing, and power of the acoustic energy transmission would be controlled as required, in response to detected natural or induced physiological events or conditions, and per known electrophysiological parameters, by the pacemaker control electronics.

A single receiver-stimulator device may be implanted as described above for single site pacing; additionally it would be possible to implant a plurality of receiver-stimulator devices which would stimulate either simultaneously by receiving the same transmitted acoustic energy, or sequentially through fixed or programmable delays after receiving the same transmitted acoustic energy, or independently by responding only to signal information of the transmitted acoustic energy of a specific character (i.e., of a certain frequency, amplitude, or by other modulation or encoding of the acoustic waveform) intended to energize only that specific device. Additional benefit of implanting receiver-stimulator devices during cardiac surgery may be obtained in their long-term utilization either for temporary pacing or for permanent pacing using either external or implantable controller-transmitter devices described in related referenced applications. Implanted receiver-stimulator devices do not have to be removed as temporary pacing leads/wires must be removed and the insertion access site closed.

In a first preferred embodiment a leadless cardiac pacemaker would be employed as a left ventricular stimulator functioning with an external controller-transmitter that is a "slave" to an external conventional (i.e., utilizing wires/electrodes) right heart pacemaker, either a single or preferably a dual chamber type. The purpose of such a slave controller-transmitter system would be to provide left ventricular pacing alone or provide left ventricular pacing synchronous with the right ventricular pacing provided by the external right heart pacemaker as a beneficial treatment for cardiac surgery patients to improve hemodynamics, but without necessitating the placement of a left ventricular lead/wire.

In such an embodiment, the receiver-stimulator would be implanted at a desired location within or on the left ventricle, preferably fully attached within the myocardium. A specialized controller-transmitter would then be externally configured with a transmitter placed at a location on the skin that allows acoustic energy transfer to the implanted receiver-stimulator (i.e., an acoustic window). The specialized "slave" controller-transmitter would connect directly to a pacing output port of the external pacemaker or would connect to a T-junction with the ventricular lead/wire connected to the external pacemaker. The slave controller-transmitter would include circuitry to detect pacing output signals from the external right heart pacemaker. The slave controller-transmitter would then respond to the pacing output signal and transmit acoustic energy to the implanted receiver-stimulator in order to produce a left ventricular stimulation at the desired time in relation to timing directed by the external pacemaker for intended ventricular paced output. For example, if the connection from the external pacemaker to a ventricular output channel is directly connected to and monitored by the slave controller-transmitter, then with each detected pacing output, a transmission occurs immediately upon this detection, a left ventricular pacing stimulus is delivered by the receiver-stimulator to the left ventricle. Further, if the ventricular output channel of the external pacemaker is connected to a right ventricular lead and the slave controller-transmitter is monitoring the output on the lead, then the transmission will be nearly simultaneous with the RV pacing output to the lead and will produce bi-ventricular pacing therapy. In this configuration, the external pacemaker would be able to use the right ventricular lead connection for sensing cardiac events using the electrodes of the lead.

Alternatively, the external controller-transmitter could be adapted to work in conjunction with an external pacemaker that contained an output specifically intended for bi-ventricular application to a left ventricular lead/wire. In this embodiment, to eliminate the requirement to place the left ventricular lead, the controller-transmitter would connect via a special wire to the external pacemaker's left ventricular output. The controller-transmitter would then detect the external pacemaker's left ventricular pacing output from the special wire and immediately transmit acoustic energy to activate the receiver-stimulator implanted into the left ventricle. Such systems would offer elimination of the left ventricular lead/wire and require only a simple controller-transmitter unburdened by associated pacemaker signal processing circuitry and algorithms.

Another preferred embodiment is a leadless stand alone external single chamber pacemaker. Such an embodiment would utilize the same or a similar implantable receiver-stimulator device as described above; however, in this case, it would be implanted into or attached to the right atrium of the heart in order to provide right atrial pacing, or implanted into or attached to either the right ventricle or left ventricle of the heart in order to provide right or left ventricular pacing, or finally multiple receiver-stimulators implanted within any single chamber. The controller-transmitter would then incorporate most or all of the features of a contemporary external single chamber pacemaker device (e.g. AOO or VOO demand pacing modes). By adapting the external device to detect atrial and/or ventricular events from ECG electrodes on the patient's skin, the device would also contain the electrogram sensing capability of a standard pacemaker (e.g., sensed cardiac events used in inhibited or triggered pacing modes AAI, AAT, VVI, or VVT). Such conventional pacemakers commonly utilize right atrial or right ventricular leads for treatment of Brady arrhythmias, or slow heart rate. A pacemaker system according to this invention would advantageously not require the use of temporary leads/wires in contact with the heart and protruding from the body. Moreover, the ability to use a left ventricular lead alone enables the potential hemodynamic benefit of left ventricular pacing compared to a right ventricular pacing without the use of leads of any kind. Further enhancement to this single chamber external pacemaker system would include other patient physiological sensor(s) that adjust the patient's paced rate in response to the sensor, e.g., motion detection. This would provide the capability for AAIR and VVIR modes of pacing.

As described previously, sensing of electrical activity in the body and other patient physiological information such as movement, blood pressure, intracavity impedance changes, or heart sounds would be provided from electrodes and/or other sensors incorporated onto or into or within the housing of the external controller-transmitter. In a particular adaptation the external transmitting transducer for the controller-transmitter may be used as a sensor for mechanical/motion sensing or for heart sound sensing.

In another preferred embodiment of the leadless cardiac pacemaker system an external dual chamber pacemaker could be constructed, with functions similar to present dual chamber (DDD mode) pacemakers. Such a pacemaker would be realized by utilizing two implantable receiver-stimulator devices and an external controller-transmitter device capable of separately activating the two receiver-stimulator devices. One receiver-stimulator device would be implanted into or attached to the right atrium as described above, the second would be implanted into or attached to the right or left ventricle. One external controller-transmitter device would transmit ultrasound to the two implanted receiver-stimulators, causing the receiver-stimulators to provide pacing stimulation to the atrium and ventricle either simultaneously or sequentially. If sequential, timed stimulation to the atrium and ventricle is required, various means to accomplish this could be incorporated into the leadless pacemaker system. In one possibility, a single acoustic waveform would be transmitted at the time necessary to activate the first, typically atrial, receiver-stimulator. The second, typically ventricular, receiver stimulator device would be of a modified design incorporating circuitry and devices to capture and temporarily store the acoustic energy transmitted at the time of atrial stimulation, and after a fixed delay provide this energy to its stimulation electrodes to pace the ventricle. Sequential stimulation could also be accomplished under direct control of the controller-transmitter, possibly utilizing the sequential transmission of acoustic energy at different frequencies, with each receiver-stimulator tuned to respond only to a single unique frequency. Other methods including amplitude modulation, frequency modulation, time-division modulation, or other modulation or encoding of the acoustic waveform would also permit selective and sequential pacing from multiple implanted receiver-stimulator devices. Alternately, two controller-transmitters transducers could be placed on the body, each configured to transmit acoustic energy only to one specific receiver-stimulator, such configuration achieved either through spatial separation, frequency separation, or other modulation or encoding means as previously described.

In such a dual chamber system, sensing of the surface ECG or other patient physiological information would be provided from electrodes and/or other sensors incorporated with connection to the housing of the external controller-transmitter. While not typical of temporary external pacemakers, further enhancement to this dual chamber pacemaker system could include other patient physiological sensor(s) that adjust the patient's paced rate in response to the sensor, e.g., respiration rates, blood pressure, and the like. This would provide the capability for DDDR modes of pacing.

It can be seen that a dual chamber pacemaker system as described above could be further adapted as a bi-ventricular pacemaker for enhancing hemodynamics or acutely treating HF. In one embodiment of a bi-ventricular pacemaker the system described above, with appropriate adaptations to the timing considerations between the two pacing signals, could be employed with one receiver-stimulator implanted into the right ventricle and the second receiver-stimulator implanted into the left ventricle. In a further enhancement, a third receiver-stimulator could be implanted into the right atrium to provide both dual chamber right-sided pacing with synchronous left ventricular pacing. As described above, means to provide proper sequencing of the multiple pacing stimuli would be employed.

Post cardiac surgery patients can have potentially lethal heart rhythms including atrial flutter, atrial fibrillation, or ventricular tachycardia and fibrillation. Having the additional capability to select the location for a cardiac lead placement for terminating episodes of arrhythmia using antitachycardia pacing techniques would be more effective compared to current devices. The advantage of terminating arrhythmic episodes with selected-site pacing may be the avoidance of painful high energy shocks. Moreover, the capability of implanting multiple receiver-stimulators in any heart chamber may allow multisite pacing for the prevention or termination of atrial fibrillation and ventricular fibrillation.

The methods and systems of the present invention may be utilized for antitachycardia pacing (ATP), including prevention algorithms, utilizing acoustic energy to transmit energy and signal information from a controller-transmitter, which is externally located, to one or more implanted receiver-stimulators having electrodes adapted to be implanted in direct contact with cardiac tissue. The acoustic controller-transmitter will usually have ECG or other monitoring means that allow detection of tachycardia.

DETAILED DESCRIPTION OF THE INVENTION

The systems and devices described comprise a controller-transmitter device that will deliver acoustic energy and information to one or more implanted receiver-stimulator device(s) that will convert the acoustic energy to electrical energy of a form that can be used to electrically pace the heart. The acoustic energy can be applied with ultrasound as a single burst or as multiple bursts with appropriate selection of the following parameters:

| Parameter | Value Range |
| --- | --- |
| Ultrasound frequency | 20 kHz-10 MHz |
| Burst Length (#cycles) | 2-10,000 |
| Stimulation Pulse Duration | 0.1 µS-10 mS |
| Duty Cycle | 0.01-0.2% |
| Mechanical Index | $\leq 1.9$ |

The controller-transmitter device would contain an ultrasound transducer or transducers of appropriate size(s) and aperture(s) to generate sufficient acoustic power and signal information to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously; it is also possible for multiple devices to function independently, either by responding only to a specific transmitted frequency, or through the use of a selective modulation technique such as amplitude modulation, frequency modulation, pulse width modulation, or through encoding techniques including time-division multiplexing. Such a pacemaker system comprising a controller-transmitter and at least one receiver-stimulator would preferably operate at an ultrasound frequency between 20 kHz and 10 MHz, and more preferably operate at a frequency between 100 kHz and 1 MHz, and most preferably operate at a frequency between 200 kHz and 500 kHz.

The signal information generated by the controller-transmitter will most often comprise pulse width and pulse amplitude information used by the receiver-stimulator to construct a corresponding electrical output. Alternatively, the signal information may comprise address information (identifying a particular receiver-stimulator device or group of devices to trigger), triggering information to initiate output (turn on or off) the receiver-stimulator device(s), delay information to control when the receiver-stimulator device(s) initiate output, the level or other characteristics of the electrical power to be delivered, and the like. The receiver-stimulator device(s) will usually have circuitry to permit decoding of the signal information (which will usually be encoded in the power transmission), and additional circuitry such as a digital gate which can turn on and off the electrical output, timer circuitry to permit a delay in turning on or off the electrical output, and the like.

The controller-transmitter device contains a transmitting transducer component which would be externally applied on the skin.

The controller-transmitter device may include sensors such as surface ECG electrodes for detecting the patient's electrogram and/or detection circuitry for detecting pacing output signals directly connected to other devices. In certain more complex embodiments additional physiological sensors may be utilized including but not limited to sensors which would detect the patient's blood pressure, temperature, respiration, and/or heart sounds. Circuitry and algorithms for utilizing these signals for control of the pacemaker function would be provided. Such electrodes and other sensors would be preferably connected to the housing of the controller-transmitter device.

The acoustic transmitter function may also be incorporated within a hybrid device providing conventional lead/wire based electrical stimulation and acoustic transmission with a variety of combinations possible. In this such system a conventional lead/electrode system would provide sensing from and stimulus to the right atrium and/or right ventricle, and the receiver-stimulator would provide synchronized stimulation to another area of the heart for example the left ventricle.

Figure 1:
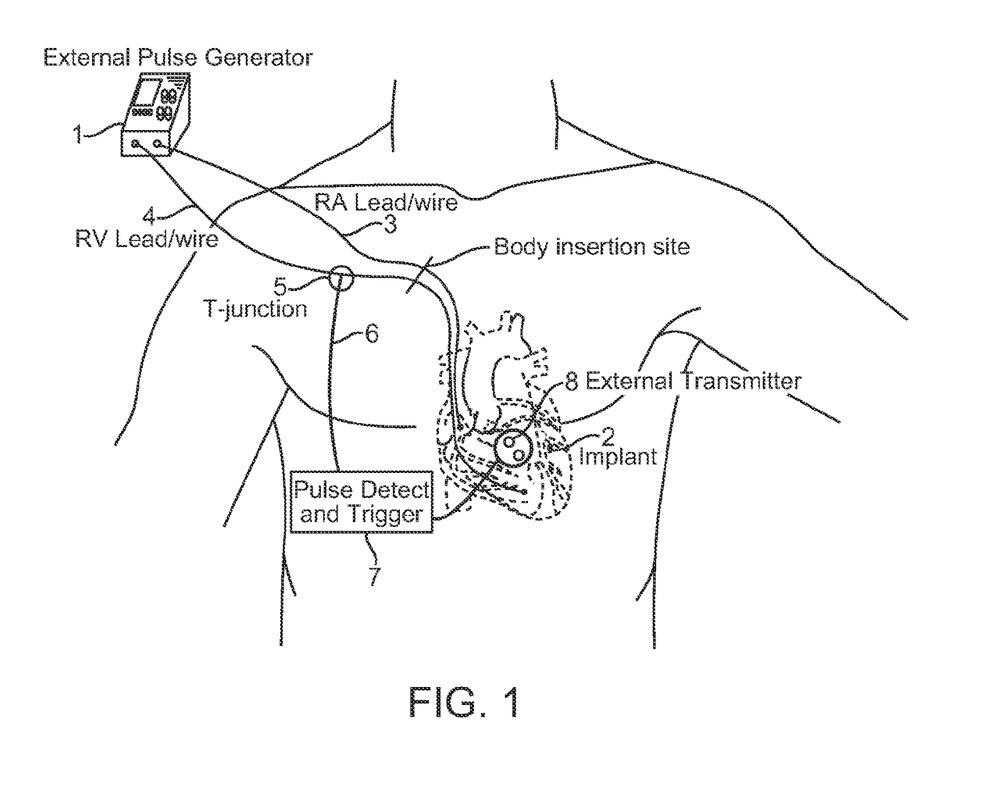
FIG. 1 illustrates an external pacemaker and temporary pacing leads used with an external controller-transmitter and an implanted receiver-stimulator in accordance with the principles of the present invention.
Figure 2:
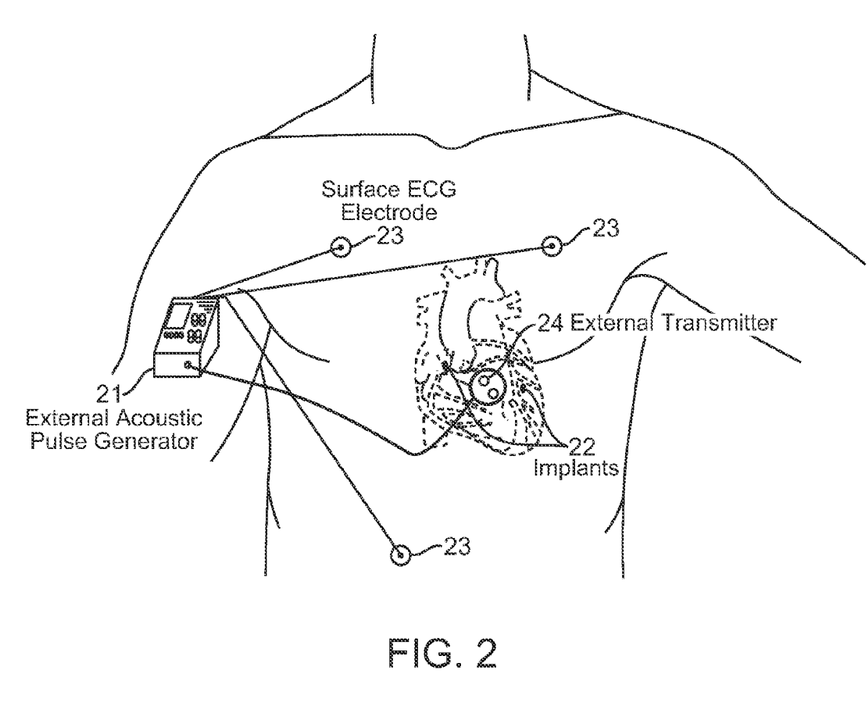
FIG. 2 illustrates an external pacemaker combining the functions of a pacemaker and the function of a controller-transmitter with multiple implanted receiver-stimulators in accordance with the principles of the present invention.

Examples of external leadless cardiac pacemaker systems are illustrated in FIGS. 1 through 2.

FIG. 1 illustrates a "slave" configuration in a biventricular pacing application in conjunction with a conventional external dual chamber pacemaker. It should be appreciated that this slave configuration is equally applicable to single chamber, dual chamber, or ATP pacing applications that would be supported by an external pacemaker in many combinations of leads/wires and receiver-stimulators contacting heart tissue. In FIG. 1, an external dual chamber pacemaker device 1 containing circuitry to provide pacing and sensing control is connected to leads 3 and 4 which are shown inserted into the right atrium and the right ventricle respectively through an access into the patient and placed through vascular means into the heart. The right ventricular lead 4 is connected through a T-junction component 5 and a cable 6 is connected to a controller-transmitter 7. Upon detection of a pacing level output signal on cable 6, an ultrasound signal is transmitted onto the surface of the patient by the controller-transmitter 7 via transmit transducer 8 through intervening tissue to the receiver-stimulator device 2, shown implanted in the left ventricle. Receiver-stimulator device 2 contains means to receive this acoustic energy and convert it into an electrical pulse which may then be applied to the attached electrodes. In this example the conventional external dual chamber pacemaker 1 utilizing both a conventional right atrial lead/wire 3 and conventional right ventricular lead/wire 4 is used to deliver pacing modalities to the right heart with the controller-transmitter 7 incorporating connections and appropriate control circuitry that allows detection of the pacing pulse output form the external pacemaker 1 and provides information whereby the control circuitry can at the proper time initiate the acoustic transmission which will result in left ventricular pacing. In this example, bi-ventricular pacing is achieved.

Modifications to the configuration of FIG. 1 can be made for many combinations utilizing an external pacemaker driving a slave controller-transmitter based detection of the pacing pulse output from the master external pacemaker FIG. 2 illustrates a stand alone configuration in a dual chamber pacing application using an external noninvasive dual chamber pacemaker. It should be appreciated that this standalone noninvasive configuration is equally applicable to single chamber, dual chamber, multi-site, or ATP pacing applications that would be supported by an external pacemaker in many combinations with receiver-stimulators contacting heart tissue. In FIG. 2 an external dual chamber pacemaker device 21 containing circuitry to provide pacing and sensing control and circuitry to generate acoustic transmission is connected to multiple surface ECG leads c, which are shown in the left arm, right arm, and right leg placement. It should be appreciated that any number of appropriate ECG leads may be utilized. Compared to the external pulse generator 1 (shown in FIG. 1), external acoustic pulse generator 21 is an integrated device with the ability to sense cardiac electrograms and generate acoustic pacing signal. The ECG leads 23 are connected to the pacemaker device 21 to provide the capability in the pacemaker device for processing a surface ECG signal and using information from the signal to provide pacing mode therapy. Based on selected setting on the control panel of the pacemaker device 21 pacing is applied by an ultrasound signal transmission onto the surface of the patient by the pacemaker device 21 via transmitter transducer 24 through intervening tissue to the receiver-stimulator devices 22, shown implanted in the right atrium and the left ventricle. Receiver-stimulator devices 22 contain means to receive this acoustic energy and convert it into an electrical pulse which may then be applied to the attached electrodes. Compared to the receiver-stimulator 2 (shown in FIG. 1), receiver-stimulator devices 22 are capable of being activated individually. The pacemaker device 21 and/or the receiver-stimulator devices 22 are adapted to trigger pacing simultaneously, synchronously, or independently. In this example, the external dual chamber pacemaker device 21 is configured to provide dual chamber pacing to the right atrium and the left ventricle.

Modifications to the configuration of FIG. 2 can be made for many combinations utilizing an external pacemaker transmitting ultrasound to one or more receiver-stimulators and utilizing sensing components to adjust pacing modalities.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A method for stimulating cardiac tissue, said method comprising:

placing a pacing lead to be in contact with a heart of a patient at a first cardiac stimulation site on a right side of the heart, implanting a leadless receiver-stimulator at a second cardiac stimulation site in a left ventricle of the heart, connecting the pacing lead to an external pacemaker, generating an electrical pacing pulse from the external pacemaker and applying the electrical pacing pulse to the pacing lead, wherein said electrical pacing pulse delivers cardiac stimulation energy to the first cardiac stimulation site, detecting the electrical pacing pulse using an externally located acoustic energy generator;

upon detecting the pacing pulse, generating acoustic energy using the externally located acoustic energy generator that is coupled to the patient; and receiving said acoustic energy by the leadless receiver stimulator at the second cardiac stimulation site, wherein said acoustic energy is converted into cardiac stimulation energy based on both energy and signal information included in the generated acoustic energy.

2. The method of claim 1, wherein receiving comprises receiving the acoustic energy at least two different cardiac stimulation sites.

3. The method of claim 2, wherein the signal information sequentially activates two receiver-stimulators to stimulate two different cardiac sites sequentially.

4. The method of claim 2, wherein the signal information simultaneously activates two receiver-stimulators to stimulate two different cardiac sites simultaneously.

5. The method of claim 1, wherein the cardiac stimulation energy is delivered to treat a cardiac arrhythmia.

6. The method of claim 1, wherein the cardiac stimulation energy is delivered to terminate cardiac arrhythmia.

7. The method of claim 1, wherein the cardiac stimulation energy is delivered to improve cardiac hemodynamics.

8. A method as in claim 1, further comprising removing the pacing lead from the patient, while leaving the implanted leadless receiver-stimulator in place.

9. A system for stimulating cardiac tissue, said system comprising:

an external pacemaker and one or more temporary pacing leads having an electrode assembly adapted to be in direct contact with cardiac tissue on a right side of a heart wherein the external pacemaker is adapted to sense cardiac activity using the pacing leads and deliver electrical pacing pulse energy sufficient to stimulate the cardiac tissue using the pacing lead;

an external acoustic controller-transmitter adapted to be connected to one or more of the pacing leads and to detect pacing level electrical signals on the pacing leads; and an implantable leadless acoustic receiver-stimulator having an electrode assembly adapted to be in direct contact with cardiac tissue in a left ventricle of the heart, wherein the controller-transmitter is adapted to transmit acoustic energy, wherein the acoustic energy is transmitted upon detecting the pacing level electrical signal by the external acoustic controller-transmitter and the receiver-stimulator is adapted to receive acoustic energy, wherein the transmission from the controller-transmitter contains energy and signal information sufficient to stimulate said cardiac tissue.

10. The system of claim 9, wherein the receiver-stimulator comprises an acoustic receiver which receives acoustic energy and generates electrical energy, means for converting the electrical energy to a direct current or waveform to stimulate the cardiac tissue, and electrodes adapted to deliver the direct current or waveform to myocardial tissue.

11. The system of claim 10, wherein the implantable receiver-stimulator and temporary pacing leads are adapted to be secured within a chamber, respectively the left ventricle and a right heart.

12. The system of claim 10, wherein the implantable receiver-stimulator and temporary pacing leads are adapted to be embedded and secured within the myocardial tissue.

13. The system of claim 10, wherein the implantable receiver-stimulator and temporary pacing leads are adapted to be secured within (1) a left ventricle and (2) the coronary veins or arteries of the heart, respectively.

14. The system of claim 9, wherein the externally applied acoustic controller-transmitter is adapted to trigger an acoustic transmission into a patient upon detecting the electrical pacing pulse signal to synchronize contraction between the left and right ventricles.

15. The system of claim 9, wherein the externally applied acoustic controller-transmitter is adapted to trigger an acoustic transmission into a patient based upon detecting the electrical pacing pulse signal to synchronize contraction within the left ventricle.

16. The system of claim 9, wherein the externally applied acoustic controller-transmitter is adapted to trigger an acoustic transmission into a patient based upon detecting the electrical pacing pulse signal to synchronize contraction between the left and right atria.

17. The system of claim 9, wherein the externally applied acoustic controller-transmitter is adapted to trigger an acoustic transmission into a patient based upon detecting the electrical pacing pulse signal to synchronize contraction between the atrium and the ventricle.

18. The system of claim 9, wherein the externally applied acoustic controller-transmitter is adapted to trigger an acoustic transmission into a patient based upon detecting the electrical pacing pulse signal to synchronize contraction between multiple sites within the heart.

19. The system of claim 9, wherein the external pacemaker and the externally applied acoustic controller-transmitter are adapted to be an integrated device.

20. The system of claim 9, wherein the externally applied acoustic controller-transmitter comprises a power source, control and timing circuitry to detect the electrical pacing signal and to trigger an acoustic transmission into a patient.

21. The system of claim 20, wherein control and timing circuitry includes one or more means for sensing physiologic variables or non-physiologic variables in order to adjust timing of the trigger.

22. The system of claim 21, wherein sensing non-physiologic variables includes detecting the electrical pacing signal and timing the trigger from that detection in order to synchronize the cardiac stimulation from the implantable receiver-stimulator with the external pacemaker.

23. The system of claim 21, wherein means for sensing physiologic variables includes a blood pressure sensor.

24. The system of claim 21, wherein means for sensing physiologic or non-physiologic variables includes an electrogram signal processor for processing signals from electrodes that are in contact with tissue.

25. The system of claim 24, wherein the electrogram signal processor is adapted to detect intrinsic cardiac beats.

26. The system of claim 25, wherein the control circuitry can selectively pace after detecting tachyarrhythmia.

27. The system of claim 24, wherein the electrogram signal processor is adapted to detect pacemaker pacing output.

28. The system of claim 24, wherein the electrogram signal processor is adapted to detect non-intrinsic cardiac beats initiated by pacemaker pacing outputs.

29. The system of claim 24, wherein the electrogram signal processor is adapted to detect tachyarrhythmia.

30. The system of claim 21, wherein means for sensing physiologic variables includes impedance sensor to detect changes in the body related to respiration cycles or lung edema.

31. The system of claim 21, wherein means for sensing physiologic variables includes a temperature sensor.

32. The system of claim 9, further comprising at least one additional receiver-stimulator device.

33. The system of claim 32, wherein the system is programmed to activate the receiver-stimulator devices sequentially.

34. The system of claim 32, wherein the system is programmed to activate the receiver-stimulator devices simultaneously.

35. The system of claim 34, wherein the external pacemaker and the external acoustic controller-transmitter are integrated into a single device.

36. The system of claim 35, wherein the external controller-transmitter/pacemaker combination comprises a power source, control and timing circuitry to deliver at least one conventional electrical pacing pulse energy signal to cardiac tissue through electrodes on the temporary pacing leads, and to trigger multiple acoustic transmissions to multiple receiver-stimulators.

37. The system of claim 9, wherein the transmitter and receiver-stimulator are adapted to transmit and receive acoustic energy wherein the frequency of the acoustic energy is between 20 kHz and 10 MHz.

38. The system of claim 37, wherein the frequency of the acoustic energy is most preferably between 800 kHz and 1.2 MHz.

39. A method for stimulating cardiac tissue, said method comprising:

generating acoustic energy at an external site on a patient synchronously with detecting a pacing pulse or electrical activity delivered to a right side of a patient's heart;

receiving said acoustic energy at a cardiac stimulation site, wherein said acoustic energy is converted into cardiac stimulation energy based on both energy and signal information included in the generated acoustic energy; and using the cardiac stimulation energy for stimulation or pacing at the cardiac stimulation site by a leadless receiver stimulator implanted in a left ventricle of the patient's heart.

40. The method of claim 39, wherein stimulating cardiac tissue provides left ventricular stimulation synchronously with right ventricular stimulation.

41. The method of claim 39, wherein stimulating cardiac tissue provides right atrial stimulation synchronously with left ventricular stimulation.

42. The method of claim 39, wherein synchronizing the cardiac tissue stimulation is performed by processing electrogram signals.

43. The method of claim 42, wherein the processing of electrogram signals and synchronizing the stimulation is performed by sensing atrial and/or ventricular electrogram signals obtained from a surface ECG.

44. The method of claim 42, wherein the processing of electrogram signals and synchronizing the stimulation is performed through a direct connection to leads in contact with the heart.

45. The method of claim 39, wherein synchronizing the stimulation is performed by detecting intrinsic or non-intrinsic cardiac beats from an electrogram signal.

46. A method as in claim 39, further comprising removing the pacing lead from the patient, while leaving the implanted leadless receiver-stimulator in place.

* * * * *